(12) United States Patent
Charlton

(10) Patent No.: US 7,927,545 B2
(45) Date of Patent: Apr. 19, 2011

(54) CONTAINERS FOR READING AND HANDLING DIAGNOSTIC REAGENTS AND METHODS FOR USING THE SAME

(75) Inventor: Steven C. Charlton, Osceola, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

(21) Appl. No.: 12/789,185

(22) Filed: May 27, 2010

(65) Prior Publication Data
US 2010/0233025 A1 Sep. 16, 2010

Related U.S. Application Data

(63) Continuation of application No. 12/077,395, filed on Mar. 19, 2008, now Pat. No. 7,749,454, which is a continuation of application No. 10/845,335, filed on May 14, 2004, now Pat. No. 7,364,699.

(60) Provisional application No. 60/479,170, filed on Jun. 18, 2003.

(51) Int. Cl.
*G01N 31/22* (2006.01)

(52) U.S. Cl. ........... 422/58; 422/56; 422/61; 422/66; 422/102; 436/44; 436/47; 436/63

(58) Field of Classification Search .......... 422/102, 422/66, 56, 58, 61; 436/44, 47, 63
See application file for complete search history.

(56) References Cited

U.S. PATENT DOCUMENTS

| 3,728,081 | A |   | 4/1973 | Bidanset .......... 23/259 |
| 3,786,510 | A |   | 1/1974 | Hodges .......... 346/33 ME |
| 4,954,319 | A | * | 9/1990 | Koizumi et al. .......... 422/67 |
| 5,120,420 | A |   | 6/1992 | Nankai et al. .......... 204/403 |
| 5,194,393 | A |   | 3/1993 | Hugl et al. .......... 436/525 |
| 5,228,972 | A | * | 7/1993 | Osaka et al. .......... 204/415 |

(Continued)

FOREIGN PATENT DOCUMENTS

DE 198 49 539 A1 5/2000

(Continued)

OTHER PUBLICATIONS

European Search Report corresponding to co-pending European patent Application Serial No. 04013401.7-1265, European Patent Office, dated Jan. 10, 2004, 3 pages.

*Primary Examiner* — Jill Warden
*Assistant Examiner* — Dwan A Gerido
(74) *Attorney, Agent, or Firm* — Nixon Peabody LLP

(57) ABSTRACT

A container with a rotatable lid for reading and handling diagnostic reagents in tape form comprising a body portion, a lid portion, a continuous tape, a reagent-sensing device, and a storage device. The body portion includes an inner and outer surface. The lid portion is attached to the body portion and is adapted to rotate from a closed position to an open position. The continuous tape includes a diagnostic reagent. The reagent-sensing device is attached to either the body portion or the lid portion and adapted to read the diagnostic reagent. The storage device is attached to the body portion that is adapted to hold and dispense an unused portion of the continuous tape. During the rotation of the lid portion, the continuous tape is advanced from the first storage device and is extended over the reagent-sensing device.

8 Claims, 1 Drawing Sheet

U.S. PATENT DOCUMENTS

| | | | | |
|---|---|---|---|---|
| 5,429,735 A | | 7/1995 | Johnson et al. | 204/403 |
| 5,505,308 A | | 4/1996 | Eikmeier et al. | 206/449 |
| 5,609,823 A | | 3/1997 | Harttig et al. | 422/66 |
| 5,645,798 A | | 7/1997 | Schreiber et al. | 422/58 |
| 5,660,791 A | | 8/1997 | Brenneman et al. | 422/58 |
| 5,679,311 A | | 10/1997 | Harttig et al. | 422/102 |
| 5,720,924 A | | 2/1998 | Eikmeier et al. | 422/102 |
| 5,759,364 A | | 6/1998 | Charlton et al. | 204/403 |
| 5,780,304 A | * | 7/1998 | Matzinger et al. | 436/169 |
| 5,788,064 A | | 8/1998 | Sacherer et al. | 206/204 |
| 5,798,031 A | | 8/1998 | Charlton et al. | 204/403 |
| 5,997,817 A | * | 12/1999 | Crismore et al. | 204/403.1 |
| 6,096,269 A | | 8/2000 | Charlton et al. | 422/58 |
| 6,176,119 B1 | | 1/2001 | Kintzig | 73/53.01 |
| 6,378,702 B1 | | 4/2002 | Kintzig | 206/456 |
| 6,988,996 B2 | | 1/2006 | Roe et al. | 600/584 |
| 7,364,699 B2 | | 4/2008 | Charlton | 422/66 |
| 7,749,454 B2 | | 7/2010 | Charlton | 422/102 |
| 2001/0042683 A1 | | 11/2001 | Musho et al. | 204/403 |
| 2002/0188224 A1 | * | 12/2002 | Roe et al. | 600/584 |
| 2003/0083685 A1 | * | 5/2003 | Freeman et al. | 606/181 |
| 2004/0258564 A1 | | 12/2004 | Charlton | 422/58 |
| 2005/0003470 A1 | * | 1/2005 | Nelson et al. | 435/14 |

FOREIGN PATENT DOCUMENTS

| | | |
|---|---|---|
| WO | WO 94/10558 | 5/1994 |
| WO | WO 02/100274 A1 | 12/2002 |

* cited by examiner

CONTAINERS FOR READING AND HANDLING DIAGNOSTIC REAGENTS AND METHODS FOR USING THE SAME

RELATED APPLICATIONS

This application is a continuation of U.S. patent application Ser. No. 12/077,395, filed Mar. 19, 2008, now issued as U.S. Pat. No. 7,749,454, which is a continuation of U.S. patent application Ser. No. 10/845,335, filed May 14, 2004, now issued as U.S. Pat. No. 7,364,699, issued Apr. 29, 2008 which claims the benefit of U.S. Provisional Application No. 60/479,170, filed Jun. 18, 2003, all of which are hereby incorporated by reference herein in their entirety.

FIELD OF THE INVENTION

The present invention relates to containers for reading and handling diagnostic reagents and methods of using the same. More specifically, the present invention relates to containers that use tape that includes diagnostic reagents, and methods of using the same.

BACKGROUND OF THE INVENTION

The quantitative determination of analytes in body fluids is of great importance in the diagnoses and maintenance of certain physiological abnormalities. For example, lactate, fructosamine, cholesterol, bilirubin, alcohol, and drugs may be monitored or tested in certain individuals. The monitored or tested body fluids may include blood, interstitial fluid, saliva, or urine. In particular, determining glucose in body fluids is important to diabetic individuals who must frequently check the glucose level in their body fluids to regulate the glucose intake in their diets.

There have been existing containers that have included reagents in tape form. These containers, however, have one or more disadvantages. For example, one disadvantage of existing containers is that the test sensors must be delivered from the container. In such containers, the used sensors are not stored in the container and, thus, may not allow for a convenient and/or safe disposal. Other disadvantages of existing containers include not (a) adequately providing protection against environmental moisture that degrades the reagent and/or (b) keeping the reagent-sensing device adequately clean and protecting it from wear and tear of normal usage.

It would be desirable to provide a container that detects an analyte concentration such as glucose that overcomes the above-noted shortcomings.

SUMMARY OF THE INVENTION

According to one embodiment, a container with a rotatable lid for reading and handling diagnostic reagents in tape form comprises a body portion, a lid portion, a continuous tape, a reagent-sensing device, and a storage device. The body portion includes an inner and outer surface. The lid portion is attached to the body portion and is adapted to rotate from a closed position to an open position. The continuous tape includes a diagnostic reagent. The reagent-sensing device is attached to either the body portion or the lid portion and adapted to read the diagnostic reagent. The storage device is attached to the body portion that is adapted to hold and dispense an unused portion of the continuous tape. During the rotation of the lid portion, the continuous tape is advanced from the first storage device and is extended over the reagent-sensing device.

According to another embodiment, a container with a rotatable lid for reading and handling diagnostic reagents in tape form comprises a body portion, a lid portion, a continuous tape, a reagent-sensing device, a first storage device, and a second storage device. The body portion includes an inner and outer surface. The lid portion is attached to the body portion and is adapted to rotate from a closed position to an open position. The continuous tape includes a diagnostic reagent. The reagent-sensing device is attached to either the body portion or the lid portion and adapted to read the diagnostic reagent. The first storage device is attached to the body portion that is adapted to hold and dispense an unused portion of the continuous tape. The second storage device is attached to the lid portion that is adapted to receive a used portion of the continuous tape. During the rotation of the lid portion, the continuous tape is advanced from the first storage device and is extended over the reagent-sensing device and received by the second storage device.

According to a further embodiment, a container with a rotatable lid for reading and handling diagnostic reagents adapted to determine glucose concentration in tape form comprises a body portion, a lid portion, a continuous tape, a reagent-sensing device, and a first storage device. The body portion includes an inner and outer surface. The lid portion is attached to the body portion and is adapted to rotate from a closed position to an open position. The continuous tape includes a diagnostic reagent to determine glucose concentration. The reagent-sensing device is attached to either the body portion or the lid portion and adapted to read the diagnostic reagent. The first storage device is attached to the body portion that is adapted to hold and dispense an unused portion of the continuous tape. During the rotation of the lid portion, the continuous tape is advanced from the first storage device and is extended over the reagent-sensing device.

According to one method, a container with a rotatable lid for reading and handling diagnostic reagents in tape form comprises providing a rotatable container. The rotatable container comprises a body portion, a lid portion, a continuous tape, a reagent-sensing device and a first storage device. The body portion includes an inner and outer surface. The lid portion is attached to the body portion. The continuous tape includes a diagnostic reagent. The reagent-sensing device is attached to either the body portion or the lid portion and adapted to read the diagnostic reagent. The first storage device is attached to the body portion and is adapted to hold and dispense an unused portion of the continuous tape. The lid is rotated from a closed position to an open position. The continuous tape is advanced from the first storage device to extend over the reagent-sensing device during the rotation of the lid portion.

BRIEF DESCRIPTION OF THE DRAWINGS

Other advantages of the invention will become apparent upon reading the following detailed description and upon reference to the drawings in which.

Figure 1:
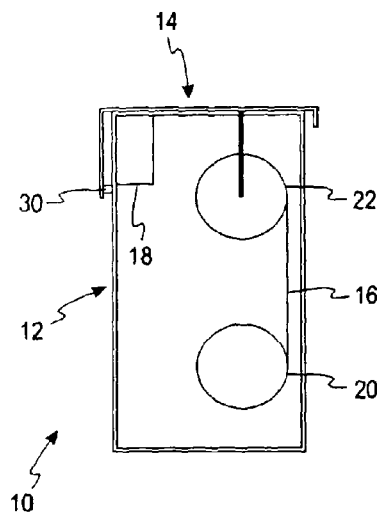
FIG. 1 is a rotatable container shown in a closed position according to one embodiment of the present invention.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DETAILED DESCRIPTION OF THE ILLUSTRATED EMBODIMENT

The present invention is directed to containers for reading and handling diagnostic reagents in tape form and methods of using the same. The diagnostic reagents may be independently selected to test one or more analytes such as glucose, lactate, fructosamine, cholesterol, bilirubin, alcohol and/or drugs. It is contemplated that other analytes may be tested using the containers of the present invention. The body fluids to be tested may include blood, interstitial fluid, saliva, or urine. It is contemplated that other fluids may be tested using the containers of the present invention. One commonly tested analyte is glucose in a whole blood sample.

The containers of the present invention comprise a body portion, a lid portion, a continuous tape, a reagent-sensing device, and a first storage device that is adapted to hold and dispense an unused portion of the continuous tape. The rotatable container provides protection against environmental moisture that degrades the reagent and keeps the reagent-sensing device clean and protects it from wear and tear of normal usage. The lid portion is adapted to rotate from a closed position to an open position where the rotation advances the continuous tape.

Figure 2:
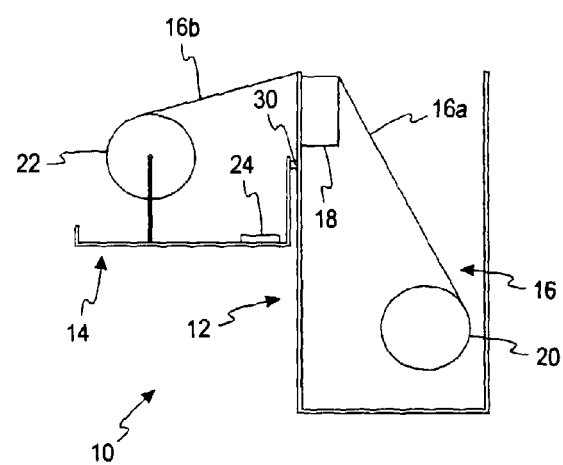
FIG. 2 is the rotatable container of FIG. 1 shown in an open position.

Referring to FIGS. 1 and 2, a rotatable container 10 is depicted in a closed position (FIG. 1) and an open position (FIG. 2). The rotatable container 10 is adapted to read and handle diagnostic reagents in tape form. The rotatable container 10 comprises a body portion 12, a lid portion 14, a continuous tape 16, and a reagent-sensing device 18. The lid portion 14 is adapted to rotate from a closed position to an open position as shown in FIGS. 1 and 2. The rotatable container may be rotated from the open position to the closed position via hinge 30. The hinge may be made of metal or may be a living hinge. Living hinges are typically made of polymeric materials that are flexible such as polypropylenes or polyethylenes. It is contemplated that the rotatable container may be moved from the open position to the closed position using other methods.

Continuous Tape

The continuous tape 16 includes a diagnostic reagent and is stored on a first storage device 20 in FIGS. 1 and 2. The first storage device 20 may be a spool or reel that is generally circular such as shown in FIGS. 1 and 2. Alternatively, the first storage device may be a polygonal shape such as a rectangle or a non-polygonal shape that is adapted to hold and dispense the continuous tape 16. It would be desirable to have a first storage device that is adapted to hold and dispense a Z-folded continuous tape. The first storage device 20 is shown attached to the body portion 12 and is adapted to hold and dispense an unused portion of the continuous tape 16. As shown in FIG. 2, the continuous tape 16 includes an unused portion 16a and a used or spent portion 16b. During the rotation of the lid portion 14 from the body portion 12, the continuous tape 16 is advanced from the first storage device 20. The continuous tape 16 is extended or pulled over the reagent-sensing device 18. The advancing of the continuous tape 16 places the unused reagent in the correct position against the reagent-sensing device 18. Thus, the opening of the lid portion 14 from the body portion 12 accomplishes (a) exposing the reagent-sensing device 18, (b) advancing the continuous tape 16 to a fresh or unused reagent area, and (c) stretching the continuous tape 16 with the reagent over the reagent-sensing device 18. When the lid portion 14 is placed in a closed position, the continuous tape 16 moves away from the reagent-sensing device 18 as shown in, for example, FIG. 1.

The continuous tape 16 may include one or more reagents to assist in determining the concentration of the amount of a fluid sample. The diagnostic reagent may be disposed in or on the continuous tape. For example, in one embodiment, the diagnostic reagent is disposed on membranes adhered to the continuous tape. The diagnostic reagent may be humidity sensitive. To determine glucose in a whole blood sample, for example, the reagent may be an enzyme such as glucose oxidase. One example of a reagent may be found in the Glucometer ENCORE® made by Bayer Corporation. Another glucose indicator reagent that may be used is glucose dehydrogenase, NAD, diaphorase, tetrazolium indicator (WST-4), and polymers. Other non-limiting examples of reagents may be used in the continuous tape. The continuous tape 16 may be made of polymeric materials, including polyethylene terephthalate (PET), polycarbonate or polystyrene. An example of a reagent on tape is one used in the CLINITEK ATLAS® automated urine chemistry analyzer made by Bayer Corporation.

According to one embodiment, the reagent is a part of the continuous tape and, thus, remains attached to the continuous tape throughout the process. According to another embodiment, the reagent may be laminated to the continuous tape such that the reagent is adapted to separate from the continuous tape. In such an embodiment, the continuous tape may be referred to as a carrier.

According to one embodiment, the rotatable container 10 further comprises a second storage device 22. The second storage device 22 may be, for example, a spool or other type of storage device adapted to receive the used or spent continuous tape. As shown in FIGS. 1 and 2, the second storage device 22 is attached to the lid portion 14. The second storage device 22 may be desirable because it provides a convenient and safe disposal for the used or spent portion of the continuous tape 16. In such an embodiment, it is desirable for the used reagent to remain on the continuous tape 16. For example, when the lid portion 14 is placed in a closed position, the used portion of the continuous tape (i.e., the portion with used or spent reagent) is placed in or on the second storage device 22.

Reagent-Sensing Device

The reagent-sensing device of the present invention is adapted to read the diagnostic reagent. The reagent-sensing device also transmits the information (e.g., glucose concentration) to the test subject.

Referring to FIGS. 1 and 2, the reagent-sensing device 18 is attached to the body portion 12. The reagent-sensing device 18 is shown as being attached to an inner surface of the body portion 12, but it is contemplated that the reagent-sensing device may be attached to an outer surface of the body portion. For example, the reagent-sensing device may be attached near or at a top outer surface edge of the body portion (i.e., the edge of the body portion closest to the lid when the lid is in a closed position). It is often desirable to locate the reagent-sensing device within the body portion 12 because it assists in keeping the reagent-sensing device clean as well as preventing or inhibiting additional wear and tear through normal usage. The reagent-sensing device 18 is protected from such conditions when the lid portion 14 is in a closed position.

According to one embodiment of the present invention, the reagent-sensing device comprises a test sensor such as an electrochemical biosensor or an optical biosensor as are known in the art. An electrochemical biosensor uses the reagent from the continuous tape that is designed to react with an analyte in the test fluid to create an oxidation current at electrodes disposed within the electrochemical biosensor. That current is directly proportional to the concentration of the analyte in the test fluid.

Examples of an electrochemical biosensor that can be used to measure glucose concentrations are those used in Bayer Corporation's Glucometer DEX® and ELITE® systems. The reagent-sensing device of these electrochemical sensors may be integrated into the body portion and the lid portion of the containers of the present invention. Electrochemical biosensors that may be used in connection with the containers of the present invention are described in U.S. Pat. Nos. 5,120,420, 5,660,791, 5,759,364, and 5,798,031, each of which is incorporated herein in its entirety. Another example of an electrochemical sensor is described in U.S. Patent Application Publication No. 2001/0042683, published on Nov. 22, 2001, which is incorporated by reference in its entirety. One or more of the electrochemical sensors may be purchased from Matsushita Electric Industrial Company. A further example of an electrochemical sensor that may be used is disclosed in U.S. Pat. No. 5,429,735, which is incorporated by reference in its entirety. It is contemplated that other electrochemical biosensors may be used in the present invention.

An optical biosensor uses a reagent from the continuous tape and is designed to produce a colorimetric reaction indicative of the concentration of the analyte in the test fluid. The colorimetric reaction is then read by a spectrophotometer incorporated into a testing instrument. An optical biosensor that may be used in connection is described in U.S. Pat. No. 5,194,393, which is incorporated herein by reference in its entirety. Another example of an optical detection device is described in U.S. Pat. No. 6,096,269, which is incorporated herein by reference in its entirety.

It is contemplated that a lancet for drawing test fluid such as blood may be integrated or coordinated with the biosensor. In one embodiment, the lancet is located on the interior of the body portion. It is contemplated that the lancet may be placed in other locations. Alternatively, a physically separated lancing device may be used.

The containers of the present invention may include a standard that calibrates and checks on the performance of the optical biosensor in the reagent-sensing device. The standard, if used in the rotatable container 10, may be mounted on the inside of the lid such that it is properly positioned in front of the reagent-sensing device 18 and protected from the environment. For example, in FIG. 2, a calibration standard 24 is shown as being attached to the lid portion. One example of a calibration standard material, is available from Edmund Industrial Optics of Barrington, N.J. and is referred to as "white reflectance standard."

It is contemplated that additional items or devices may be located within the body portion 12. For example, to assist in maintaining a low humidity, a desiccant may be added within the body portion 12. A low humidity environment is desirable to protect at least the continuous tape with reagent. Non-limiting examples of suitable desiccants that may be used are a molecular sieve and silica gel. One type of desiccant material that may be used is 13X synthetic molecular sieves from Multisorb Technologies Inc. of Buffalo, N.Y., available in powder, pellet, and bead forms. Another desiccant that may be used is type 4A synthetic molecular sieves available from Multisorb Technologies Inc. of Buffalo, N.Y. or Texas Technologies Inc. of Leander, Tex. It is contemplated that other desiccants known in the art may be used in the present invention.

To assist in preventing or inhibiting moisture vapor ingress, at least one seal may be attached to either body portion 12 or the lid portion 14 such that the seal is located between the body portion 12 and the lid portion 14 when the lid portion is in a closed position. The seal may be attached by, for example, an adhesive or thermal welding or it may be a part of the body portion or the lid portion. The seal may be deformed when the lid portion 14 is in a closed position. The seal geometry may be optimized to minimize water vapor transmission by extending the length of the diffusion path. It is desirable for the seal to avoid accommodating a continuous tape sliding therethrough because of the potential for leaks to occur at such a location. Seals may be made from a variety of materials including, but not limited to, polymeric materials. Some desirable attributes of a material for forming the seal are high barrier properties (e.g., those with low moisture vapor transmission rates), lubricity for easy opening and closing, and elasticity for allowing the mating surfaces to conform. One non-limiting example of a polymeric material is a polyolefin such as polypropylene. The seal may be made from other materials such as elastomeric materials. Some materials for forming the seal may include cellular rubber, styrene elastomers, polyolefin elastomers, polyamide elastomers, polyester elastomers, polyurethane elastomers, and combinations thereof.

Figure 3:
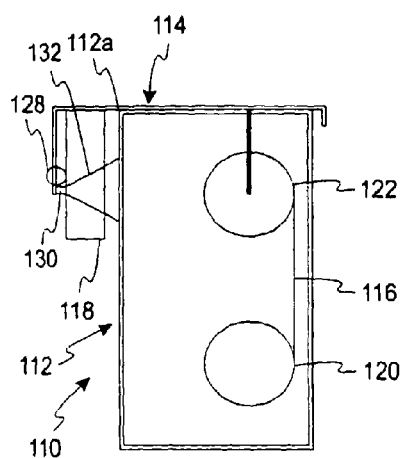
FIG. 3 is a rotatable container shown in a closed position according to another embodiment of the present invention.
Figure 4:
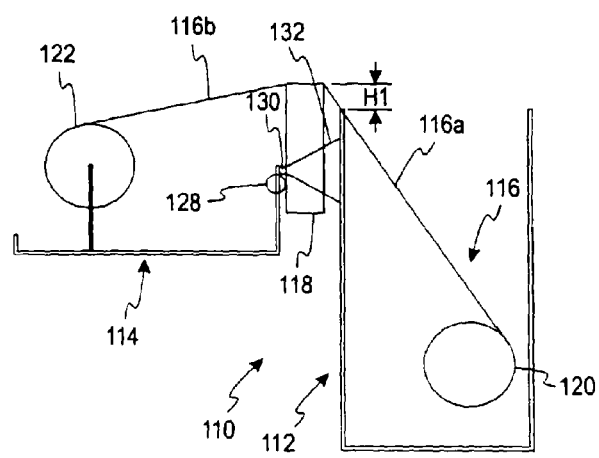
FIG. 4 is the rotatable container of FIG. 3 shown in an open position.

According to another embodiment, a rotatable container 110 is depicted in a closed position (FIG. 3) and an open position (FIG. 4). The rotatable container 110 is adapted to read and handle diagnostic reagents in tape form. The rotatable container 110 comprises a body portion 112, a lid portion 114, a continuous tape 116, and a reagent-sensing device 118. The continuous tape 116 may be the same as described above with respect to the continuous tape 16. Similarly, the reagent-sensing device 118 may be the same as described above with the reagent-sensing device 18 except with its location on the rotatable container. In this embodiment, the reagent-sensing device 118 is movably attached between the lid portion 114 and the body portion 112. In the closed position, the reagent-sensing device 118 is adjacent to an inner surface of the lid portion such that the reagent-sensing device 118 remains clean and protected from conditions such as dust and dirt. It is contemplated that the reagent-sensing device may be attached at other locations.

The rotatable container 110 further comprises a first storage device 120 and a second storage device 122. The lid portion 114 is adapted to rotate from a closed position to an open position as shown in FIGS. 3 and 4. The rotatable container may be rotated from the open position to the closed position via hinge 130 or a living hinge. The hinge 130 according to one embodiment is attached to the body portion 112 via a hinge support bracket 132. It is contemplated that the rotatable container may be moved from the open position to the closed position using other methods.

Referring still to FIGS. 3 and 4, the reagent-sensing device 118 is located external to the body portion 112 and is attached to the lid portion 114. One advantage of the rotatable container 110 is that the location of the reagent-sensing device 118 allows additional space to integrate the lancet, if used, with the reagent-sensing device 118. The reagent-sensing device 118 may be moved forward (i.e., upwardly in FIGS. 3 and 4) by a mechanism such a rack and pinion drive 128 or a cam mechanism that, for example, is operated by a hinge. The first position of the reagent-sensing device 118 (see FIG. 3) is at approximately the same height as the top edge 112a of the body portion 112. The second position of the reagent-sensing device 118 (see FIG. 4) is above the top edge of the body portion 112 by a height H1. The height H1 may vary but is generally from about 0.2 to about 0.4 inches. It is desirable to have the reagent-sensing device extend at least about 0.2 inches above the top edge 112a so as to assist the test subject in placing the test fluid on the continuous tape 116. Additionally, such a height may also assist placing the continuous tape against the reagent-sensing device such that the continuous tape is flat against the reagent-sensing device.

As discussed above, the rotatable container 110 may further include a standard to calibrate and check on the performance of the optical biosensor, if used, of the reagent-sensing device. The rotatable container 110 may also include a desiccant and seals.

The base portion and the lid portion of the rotatable containers may be made of materials having very low water vapor transmission rates. Some examples of such materials are polymeric materials including, but not limited to, polyethylene, polypropylene or metals such as aluminum. Additionally, it is contemplated that the individual properties of the base portion, the lid portion and seal are desirably optimized and do not have to be made of the same materials. It is desirable that the base portion and the lid portion in the closed position form a sealed container adapted to store humidity-sensitive diagnostic reagents.

Methods of the Present Invention

The methods for determining the analyte concentrations (e.g., glucose concentrations) may be performed by the test subjects, especially those who are diabetic. It is also contemplated that the methods may be performed by hospital or clinic personnel.

According to one method, the lid portion is rotated with respect to the body portion to an open position by the test subject. During the rotation of the lid portion from the body portion, (a) the reagent-sensing device is exposed, (b) the continuous tape is advanced to a fresh or unused reagent area, and (c) the continuous tape is positioned with the fresh or unused reagent over the reagent-sensing device. The fluid sample (e.g., a whole blood sample) is placed in contact with the unused portion continuous tape that includes a reagent and is located over the reagent-sensing device. The whole blood sample may be generated by a lancing device such as Bayer's MICROLET® adjustable lancing device. The lancing device may obtain blood by, e.g., pricking a person's finger. It is desirable to use a low volume of blood such as less than 1 μl. The reagent-sensing device determines the concentration of the analyte in the fluid sample (e.g., glucose concentration) and returns this information to the test subject. It is desirable to return this information to the test subject in a short time frame such as from about 5 to about 15 seconds.

To protect the reagent of the unused portion of the continuous tape and the reagent-sensing device, the lid portion of the container is closed by the test subject upon completion of the testing. During the closing of the lid portion, (a) the continuous tape is moved away from the reagent-sensing device and (b) the reagent-sensing device is protected. Additionally, during the closing of the lid portion, the body portion is desirably sealed to prevent or inhibit moisture vapor transmission from entering thereto. It is also contemplated that if a second storage device is included in the rotatable container, then the closing of the lid portion may advance or wind the used portion of the continuous tape onto or in the second storage device.

In another method, the rotation of the lid portion from the body portion to the open position may move the reagent-sensing device forward to a location above the top edge of the body portion. Such a movement assists the test subject in placing the test fluid on the unused portion of the continuous tape over the reagent-sensing device.

While particular embodiments and applications of the present invention have been illustrated and described, it is to be understood that the invention is not limited to the precise construction and compositions disclosed herein and that various modifications, changes and variations may be apparent from the foregoing descriptions without departing from the spirit and scope of the invention as defined in the appended claims.

What is claimed is:

1. A sensor system for determining a glucose concentration of a fluid sample, the sensor system comprising:
   an optical reagent-sensing device; and
   a container including first and second rotatable storage devices having a continuous tape extending from the first rotatable storage device, past the optical reagent-sensing device, to the second rotatable storage device such that the first rotatable storage device holds and dispenses unused portions of the continuous tape and the second rotatable storage device holds and receives used portions of the continuous tape, the container further including a desiccant and a white-reflectance calibration standard, the calibration standard operative to calibrate the optical reagent-sensing device, the continuous tape including a diagnostic reagent and a polymer material,
   wherein the optical reagent-sensing device is operative to read the diagnostic reagent such that a glucose concentration for a fluid sample is determined in approximately 5 to 15 seconds.

2. The sensor system of claim 1, wherein the calibration standard is located within the container.

3. The sensor system of claim 1, wherein the container further includes at least one seal to assist in limiting moisture from entering into the container.

4. The sensor system of claim 1, wherein the diagnostic reagent is disposed on the continuous tape.

5. The sensor system of claim 1, wherein the continuous tape further includes a plurality of membranes attached thereto, the diagnostic reagent being disposed on the plurality of membranes.

6. The sensor system of claim 1, wherein diagnostic reagent is disposed in the continuous tape.

7. The sensor system of claim 1, wherein the continuous tape is flat against at least a portion of the optical reagent-sensing device.

8. The sensor system of claim 1, wherein the optical reagent-sensing device is operative to read the diagnostic reagent to determine the analyte concentration of a fluid sample having a volume of less than 1 microliter.

* * * * *